United States Patent
Gemoules

(10) Patent No.: US 9,016,863 B2
(45) Date of Patent: *Apr. 28, 2015

(54) SCLERAL CONTACT LENS MANUFACTURING

(71) Applicant: Gregory Gemoules, Coppell, TX (US)

(72) Inventor: Gregory Gemoules, Coppell, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/159,281

(22) Filed: Jan. 20, 2014

(65) Prior Publication Data

US 2014/0132915 A1 May 15, 2014

Related U.S. Application Data

(63) Continuation of application No. 13/277,139, filed on Oct. 19, 2011, now Pat. No. 8,632,188.

(51) Int. Cl.

| | |
|---|---|
| *G02C 7/04* | (2006.01) |
| *A61B 3/125* | (2006.01) |
| *A61B 3/107* | (2006.01) |
| *B23B 5/36* | (2006.01) |
| *G02C 7/02* | (2006.01) |
| *A61B 3/103* | (2006.01) |

(52) U.S. Cl.
CPC ............. *G02C 7/047* (2013.01); *A61B 3/125* (2013.01); *A61B 3/107* (2013.01); *Y10T 82/2502* (2015.01); *B23B 5/36* (2013.01); *G02C 7/027* (2013.01); *A61B 3/103* (2013.01); *G02C 2202/20* (2013.01)

(58) Field of Classification Search
CPC ........ A61B 3/107; A61B 3/125; G02C 7/027; G02C 7/047
USPC ......... 351/200, 204, 205, 212, 219, 246, 247, 351/159.23, 159.74
See application file for complete search history.

(56) References Cited

U.S. PATENT DOCUMENTS

| | | |
|---|---|---|
| RE38,839 E | 10/2005 | Magnante |
| 7,862,176 B2 | 1/2011 | Gemoules et al. |
| 8,632,188 B1 * | 1/2014 | Gemoules ............ 351/247 |
| 2006/0264917 A1 | 11/2006 | Tuan et al. |

* cited by examiner

*Primary Examiner* — Huy K Mai

(74) *Attorney, Agent, or Firm* — Yee & Associates, P.C.

(57) ABSTRACT

The different illustrative embodiments provide a method, computer program product, and apparatus for manufacturing a scleral contact lens. A number of dimensions for the scleral lens is generated based on a shape of an eye. An alteration to a first wavefront of light caused by the first wavefront of light traveling through a pupil of the eye is identified. A modification configured to be made to a posterior surface of the scleral lens is generated based on the alteration. The modification removes the alteration for a second wavefront of light traveling through the scleral lens and the pupil of the eye.

20 Claims, 8 Drawing Sheets

FIG. 4

| NORMALIZED ZERNIKE COEFFIECIENTS IN MICRONS @ 4.60 mm ||
|---|---|
| 0 | 0.0515637347 |
| 1 | -0.6675799289 |
| 2 | -1.4029607052 |
| 3 | -0.0834998849 |
| 4 | 0.4196686886 |
| 5 | -0.0782078148 |
| 6 | -0.1467463375 |
| 7 | 0.0122578491 |
| 8 | -0.1979198393 |
| 9 | -0.1010711517 |
| 10 | -0.0967000822 |
| 11 | -0.0476730491 |
| 12 | 0.1226148000 |
| 13 | 0.2190442899 |
| 14 | 0.2567216094 |
| 15 | 0.0474184271 |
| 16 | -0.0086998066 |
| 17 | 0.0914472943 |
| 18 | 0.1115276033 |
| 19 | 0.1000700086 |
| 20 | 0.1187018439 |
| 21 | -0.0514290582 |
| 22 | -0.0229306835 |
| 23 | 0.0061440942 |
| 24 | -0.1240291564 |
| 25 | -0.0857957369 |
| 26 | -0.1061807430 |
| 27 | -0.0850744106 |
| 28 | 0.0252614995 |
| 29 | -0.0074895115 |
| 30 | 0.0171140584 |
| 31 | -0.0283845352 |
| 32 | -0.0329555546 |
| 33 | -0.0286636774 |
| 34 | -0.0334296981 |
| 35 | -0.0301801359 |
| 36 | -0.0012709067 |
| 37 | 0.0177701164 |
| 38 | 0.0186305286 |
| 39 | 0.0034803528 |
| 40 | 0.0243328085 |

FIG. 5

| | A | B | C | D | E | F | ... | AV | AW | AX |
|---|---|---|---|---|---|---|---|---|---|---|
| 1 | r | p | θ | 0 | 1 | 2 | ... | 44 | SUM (μ) | SUM (mm) |
| 2 | | 2.6000000 | 0.0000000 | -0.07853013 | -0.04447332 | 0.357348882 | ... | -0.01420905 | 0.0000000 | 0.0000000 |
| 3 | 0.0000000 | 0.0000000 | -0.0785301 | -0.0785301 | 0.0000000 | 0.0000000 | ... | 0.0000000 | 0.0016184 | 0.0000016 |
| 4 | 0.0100000 | 0.0038462 | | -0.0785301 | 0.0000000 | 0.0027488 | ... | 0.0000000 | 0.0033738 | 0.0000034 |
| 5 | 0.0200000 | 0.0076923 | | -0.0785301 | 0.0000000 | 0.0054977 | ... | 0.0000000 | 0.0052661 | 0.0000053 |
| 6 | 0.0300000 | 0.0115385 | | -0.0785301 | 0.0000000 | 0.0082465 | ... | 0.0000000 | 0.0072948 | 0.0000073 |
| 7 | 0.0400000 | 0.0153846 | | -0.0785301 | 0.0000000 | 0.0109954 | ... | 0.0000000 | 0.0094598 | 0.0000095 |
| 8 | 0.0500000 | 0.0192308 | | -0.0785301 | 0.0000000 | 0.0137442 | ... | 0.0000000 | 0.0117604 | 0.0000118 |
| 9 | 0.0600000 | 0.0230769 | | -0.0785301 | 0.0000000 | 0.0164930 | ... | 0.0000000 | 0.0141963 | 0.0000142 |
| 10 | 0.0700000 | 0.0269231 | | -0.0785301 | 0.0000000 | 0.0192419 | ... | 0.0000000 | 0.0167669 | 0.0000168 |
| 11 | 0.0800000 | 0.0307692 | | -0.0785301 | 0.0000000 | 0.0219907 | ... | 0.0000000 | 0.0194718 | 0.0000195 |
| 12 | 0.0900000 | 0.0346154 | | -0.0785301 | 0.0000000 | 0.0247395 | ... | 0.0000000 | 0.0223102 | 0.0000223 |
| 13 | 0.1000000 | 0.0384615 | | -0.0785301 | 0.0000000 | 0.0274884 | ... | 0.0000000 | 0.0252815 | 0.0000253 |
| 14 | 0.1100000 | 0.0423077 | | -0.0785301 | 0.0000000 | 0.0302372 | ... | 0.0000000 | 0.0283850 | 0.0000284 |
| 15 | 0.1200000 | 0.0461538 | | -0.0785301 | 0.0000000 | 0.0329861 | ... | 0.0000000 | 0.0316200 | 0.0000316 |
| 16 | 0.1300000 | 0.0500000 | | -0.0785301 | 0.0000000 | 0.0357349 | ... | 0.0000000 | 0.0349857 | 0.0000350 |
| 17 | 0.1400000 | 0.0538462 | | -0.0785301 | 0.0000000 | 0.0384837 | ... | 0.0000000 | 0.0384812 | 0.0000350 |
| 18 | 0.1500000 | 0.0576923 | | -0.0785301 | 0.0000000 | 0.0412326 | ... | 0.0000000 | 0.0421056 | 0.0000421 |
| 19 | 0.1600000 | 0.0615385 | | -0.0785301 | 0.0000000 | 0.0439814 | ... | | | |

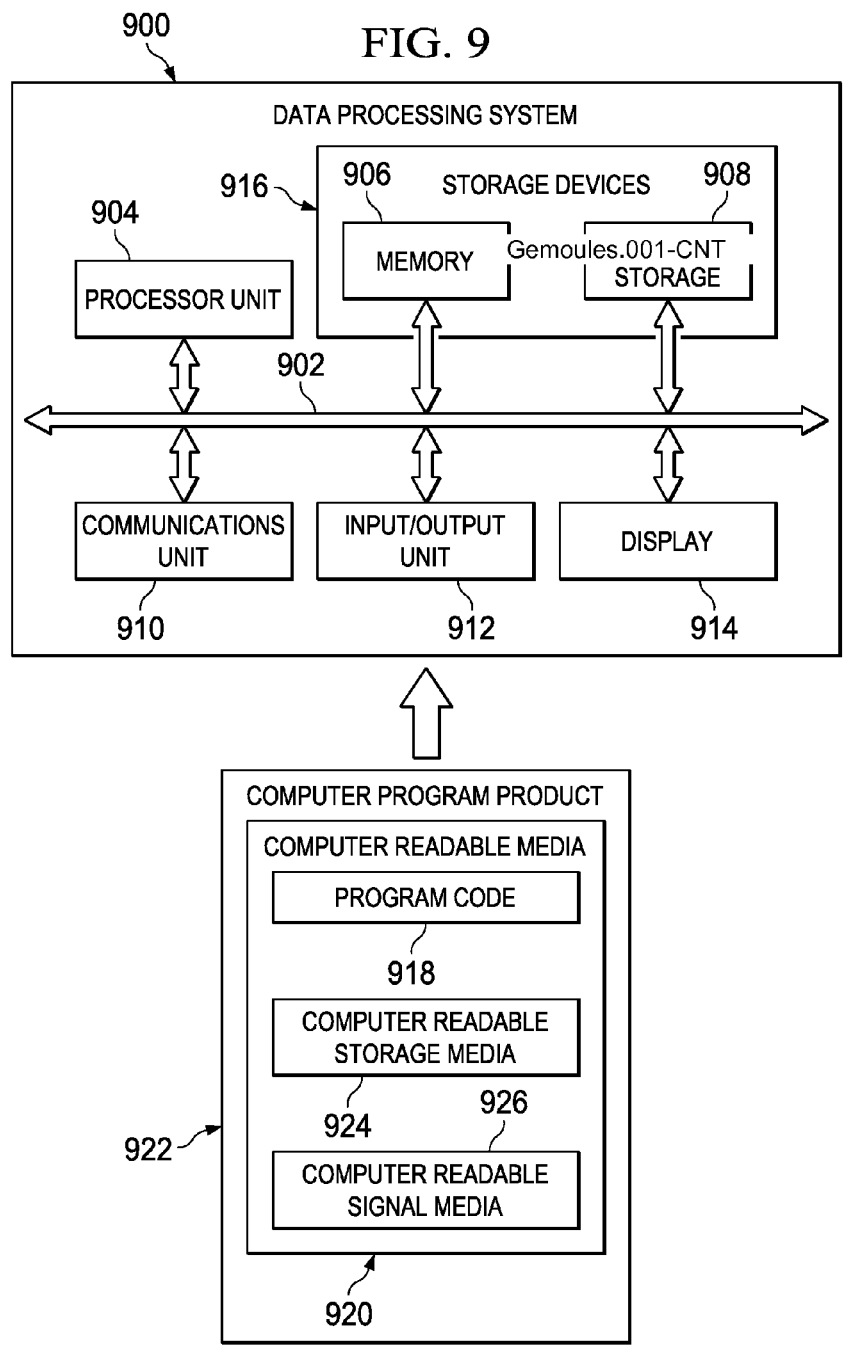

SCLERAL CONTACT LENS MANUFACTURING

This application is a continuation of U.S. application Ser. No. 13/277,139, filed Oct. 19, 2011.

BACKGROUND

1. Field

The disclosure relates generally to contact lenses. More specifically, the disclosure relates to scleral lenses. Even more specifically, the disclosure relates to a method, computer program product, and apparatus for manufacturing scleral lenses.

2. Description of the Related Art

Inconsistencies are commonly present in the human eye that causes images on the retina to be blurred and/or have less detail than images on a retina in an eye without inconsistencies. Inconsistencies in the eye are referred to as aberrations. Lower order aberrations are inconsistencies based on refractive error. For example, lower order aberrations may cause commonly experienced conditions, such as nearsightedness, farsightedness, or other suitable conditions.

Higher order aberrations are less commonly experienced than lower order aberrations. Higher order aberrations are inconsistencies in the human eye that alter a wavefront of light as the wavefront of light travels through the pupil of the eye. For example, a higher order aberration may be coma, spherical aberration, trefoil, or another suitable condition. A wavefront is a surface containing points affected in the same way by a wave at a given time. The higher order aberrations may cause glare, starburst patterns in the image, double vision, or other suitable effects.

Some inconsistencies may be reduced or eliminated by positioning a contact lens on the eye. For example, corneal contact lenses may be used to reduce or eliminate some lower order aberrations. Corneal contact lenses are contact lenses that are shaped to rest on the cornea area of the eye without resting on the pupil area of the eye. The positioning of corneal contact lenses on the eye may not eliminate higher order aberrations or reduce the higher ordered aberrations to desired levels. Further, the positioning of the corneal contact lenses on the eye may cause alteration of one or more wavefronts of light traveling through the corneal contact lens and the pupil of the eye to form additional higher order aberrations.

Scleral contact lenses are another type of contact lens. A scleral contact lens is shaped to rest on the sclera of the eye without resting on the cornea or the pupil of the eye. In other words, the scleral contact lens rests on the sclera and vaults the cornea and the pupil of the eye.

SUMMARY

The different illustrative embodiments provide a method, computer program product, and apparatus for manufacturing a scleral contact lens. A number of dimensions for the scleral lens is generated based on a shape of an eye. An alteration to a first wavefront of light caused by the first wavefront of light traveling through a pupil of the eye is identified. A modification configured to be made to a posterior surface of the scleral lens is generated based on the alteration. The modification removes the alteration for a second wavefront of light traveling through the scleral lens and the pupil of the eye.

BRIEF DESCRIPTION OF THE SEVERAL VIEWS OF THE DRAWINGS

FIG. 4 depicts an illustration of coefficients for Zernike polynomials in accordance with an illustrative embodiment;

FIG. 5 depicts an illustration of a modification represented in table form in accordance with an illustrative embodiment;

FIG. 9 depicts an illustration of a computer system in accordance with an illustrative embodiment.

DETAILED DESCRIPTION

Figure 1:
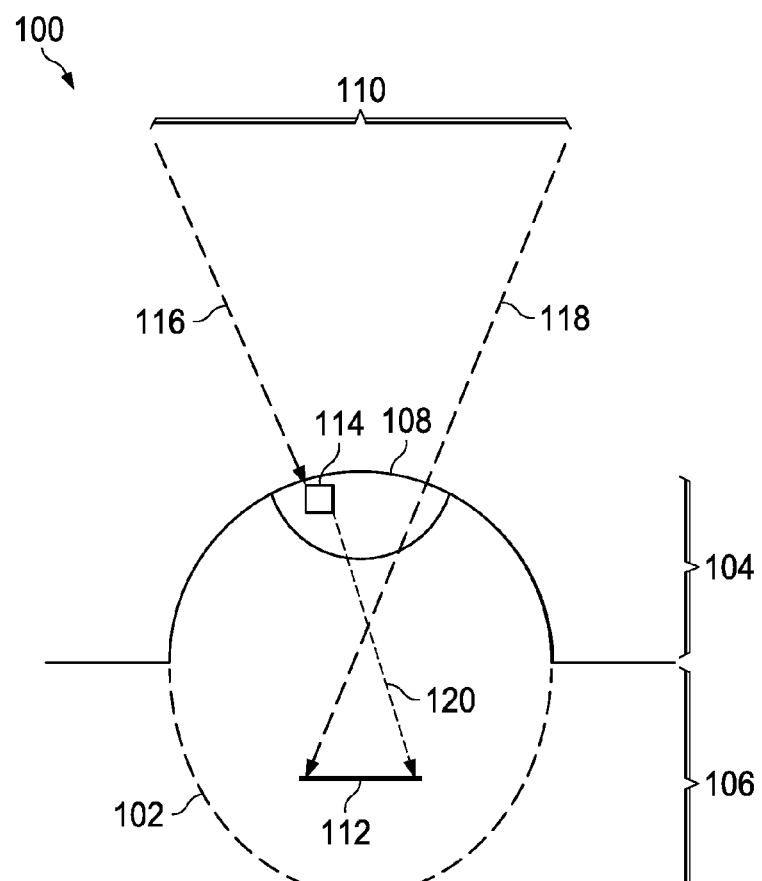
FIG. 1 depicts an illustration of a face in accordance with an illustrative embodiment.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

With reference now to FIG. 1, an illustration of a face is depicted in accordance with an illustrative embodiment. Face 100 is an example of the face of patient 204 in FIG. 2.

Face 100 includes eye 102 in this illustrative embodiment. Face 100 is a human face in the illustrative examples. Eye 102 is located on face 100 such that portion 104 may be contacted by air, while portion 106 is within face 100 such that portion 106 is not contacted by air. Pupil 108 is located in portion 104 of eye 102. Pupil 108 is a substantially round passage in eye 102 that allows light 110 to enter eye 102 and be absorbed by other components of eye 102, such as retina 112.

In this illustrative embodiment, light 110 travels through pupil 108 having inconsistency 114 and onto retina 112. Retina 112 is a layer of cells that trigger nerve activity when retina 112 is stimulated by light. In other words, retina 112 is stimulated by light 110 contacting retina 112 to produce sight imagery. Light 110 includes wavefront 116 and wavefront 118 in this illustrative embodiment. Of course, light 110 may include additional wavefronts in other illustrative embodiments. Wavefront 116 and wavefront 118 are surfaces containing points affected in the same way by a wave of light 110 at a given time.

Wavefront 118 travels through pupil 108 and on to retina 112 while traveling at a particular speed. Wavefront 116, however, travels through inconsistency 114 as wavefront 116 travels through pupil 108 and onto retina 112. In this illustrative embodiment, traveling through inconsistency 114 causes wavefront 116 to slow down. Thus, wavefront 116 reaches retina 112 at a later time as segment 120 than wavefront 118 that did not travel through inconsistency 114 as wavefront 118 traveled through pupil 108.

By traveling through inconsistency 114, wavefronts of light 110 do not reach retina 112 at about the same time. Thus, the image that is generated by light 110 and retina 112 may have undesired blurring, halo effects, less sharpness than desired, or other suitable results.

The different illustrative embodiments recognize and take into account a number of different considerations. For example, the different illustrative embodiments recognize and take into account that corneal contact lenses may not eliminate or reduce higher order aberrations in an eye to desired levels. Further, the corneal contact lenses may be undesirable to individuals because the lens may cause irritation. For example, a corneal contact lens may cause irritation and/or insufficient reduction of higher order aberrations in an eye with a keratoconus, pellucid marginal degeneration, penetrating keratoplasty, radial keratotomy or other suitable states or conditions.

The different illustrative embodiments also recognize and take into account that scleral lenses may provide a more comfortable fit without irritation of the eye to patients that experience irritation of the eye while wearing corneal contact lenses. The different illustrative embodiments provide a scleral lens that rests on the sclera and/or conjunctiva of the eye, which may be less sensitive to irritation of the eye than the corneal lens that rests on the cornea. The scleral lens curves over the cornea and pupil of the eye without contacting the cornea or the pupil. In the illustrative embodiments, fluid may be present in a space located between the lens and the eye. Further, scleral lenses may be designed to be non-rotationally symmetrical. In other words, the scleral lens may be designed to return to a particular rotation and/or position after movement in the eye. For example, the scleral lens may be moved by the person during placement or adjustment of the scleral lens.

The different illustrative embodiments also recognize and take into account that measurements generated by a wavefront aberrometer may be used to identify aberrations in the eye. A wavefront aberrometer measures the alteration to wavefronts at a plurality of different areas of the eye as the wavefronts travel into the eye. In the different illustrative embodiments, the measurements are described in terms of Zernike polynomials or another suitable orthonormal basis function. The measurements include coefficients for the Zernike polynomials, which are a mathematical description of the alteration to the wavefronts traveling into the different areas of the eye.

The different illustrative embodiments further recognize and take into account that a modification applied to the posterior surface of a scleral lens reduces the effect of variable eye conditions, such as tear film thickness, dryness of the eye surface, and other suitable conditions. Such variable conditions may cause the effect of a modification applied to the anterior surface of the lens to increase or decrease. For example, as tear film thickness increases, the effect of a modification applied to the anterior surface of the lens may be reduced. The different illustrative embodiments recognize and take into account that such variation in the effect of the modification does not occur when the modification is applied to the posterior surface of the lens.

The different illustrative embodiments also recognize and take into account that applying modifications to the posterior surface of a scleral lens to reduce or eliminate an aberration allows the lens to be designed with greater differences in thickness between the modifications as compared to modifications applied to the anterior surface of a corneal lens. The greater differences in thickness allow an increased tolerance in manufacturing the scleral lens. Thus, the cost of manufacturing the lens is reduced because less waste occurs due to lenses being manufactured that do not meet desired tolerances.

Thus, the different illustrative embodiments provide a method, computer program product, and apparatus for manufacturing a scleral contact lens. A number of dimensions for the scleral lens is generated based on a shape of an eye. An alteration to a first wavefront of light caused by the first wavefront of light traveling through a pupil of the eye is identified. A modification configured to be made to a posterior surface of the scleral lens is generated based on the alteration. The modification removes the alteration for a second wavefront of light traveling through the scleral lens and the pupil of the eye.

Figure 2:
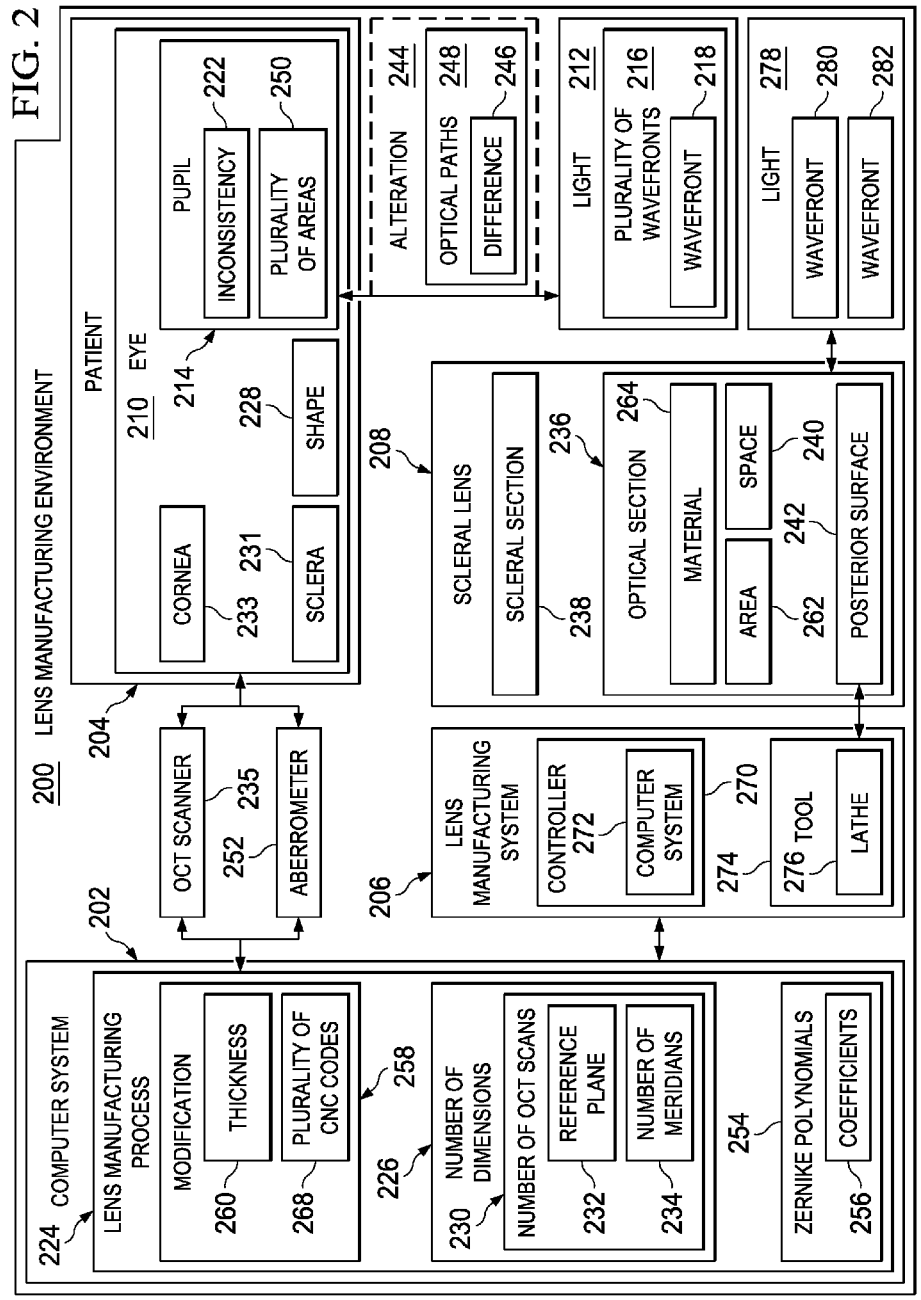
FIG. 2 depicts an illustration of a lens manufacturing environment in accordance with an illustrative embodiment.

Turning now to FIG. 2, an illustration of a lens manufacturing environment is depicted in accordance with an illustrative embodiment. Lens manufacturing environment 200 is an example of an environment in which illustrative embodiments may be implemented.

Lens manufacturing environment 200 includes computer system 202, patient 204, lens manufacturing system 206, and scleral lens 208 in this illustrative embodiment. Patient 204 is a human having at least one eye 210. Eye 210 is an organ located in the head of patient 204 that provides vision to patient 204 by allowing light 212 to enter pupil 214 of eye 210. Pupil 214 is a substantially round passage in eye 210 that allows light 212 to enter eye 210 and be absorbed by other components of eye 210, such as the retina and other suitable components.

Light 212 includes plurality of wavefronts 216. A plurality of an item, as used herein, means two or more of the item. For example, plurality of wavefronts 216 means two or more wavefronts. Wavefront 218 is a wavefront in plurality of wavefronts 216. Wavefront 218 is a collection of points or a surface along which waves of light have the same phase. Wavefront 218 travels into eye through pupil 214. In this illustrative embodiment, pupil 214 has inconsistency 222. Inconsistency 222 is a portion of pupil 214 that causes wavefront 218 to be altered as wavefront 218 travels through pupil 214. Of course, pupil 214 may have multiple inconsistencies in some illustrative embodiments.

Computer system 202 is an example implementation of data processing system 900 in FIG. 9. Computer system 202 runs lens manufacturing process 224 in this illustrative embodiment. Lens manufacturing process 224 generates number of dimensions 226. Number of dimensions 226 is a collection of numeric values and/or functions that represent the measurements of scleral lens 208.

Lens manufacturing process 224 measures shape 228 of eye 210 to generate number of dimensions 226. In this illustrative embodiment, lens manufacturing process 224 measures shape 228 using number of optical coherence tomography (OCT) scans 230 using optical coherence tomography scanner 235. An example of an optical coherence tomography scan is optical coherence tomography scan 300 in FIG. 3. In other illustrative examples, a pentacam scan, an interferometer scan, a scleral topography scan, or another suitable scan may be used.

Reference plane 232 on eye 210, such as a particular distance above the center of pupil 214, is selected. Lens manufacturing process 224 then performs number of optical coherence tomography scans 230 on eye 210 by using backscattering of light from eye 210. In these illustrative examples, a scan is performed from the apex of the cornea of eye 210 into sclera 231 of eye 210. Sclera 231 is a layer of eye 210 that surrounds cornea 233 of eye 210. Cornea 233 is a layer of eye 210 that covers the iris and pupil 214 of eye 210.

Lens manufacturing process 224 identifies the backscattering of light to identify a distance from reference plane 232 to points on eye 210. In some illustrative embodiments, additional optical coherence tomography scans 230 are performed along number of meridians 234 to generate additional dimensions for number of dimensions 226. Number of meridians 234 are paths that extend across eye 210. Lens manufacturing process 224 may also generate additional dimensions for number of dimensions 226 by interpolating measured distances. For example, lens manufacturing process 224 may use bicubic splines, tension splines, constrained splines, polynomial splines, or another suitable mathematical process to perform the interpolation.

Lens manufacturing process 224 then designates a portion of scleral lens 208 to be optical section 236 and a portion of scleral lens 208 to be scleral section 238. Scleral section 238 is a portion of scleral lens 208 that contacts sclera 231 of eye 210 when scleral lens 208 is positioned on eye 210. Optical section 236 is a portion of scleral lens 208 that is surrounded by scleral section 238 and extends above pupil 214 of eye 210. In other words, optical section 236 does not contact pupil 214 when scleral lens 208 is positioned on eye 210.

Space 240 is present between pupil 214 and optical section 236. Space 240 may contain eye fluids, air, or another suitable substance. In some illustrative examples, the apex of optical section 236 is located along reference plane 232. Thus, optical section 236 forms a curve over pupil 214 with an anterior surface and posterior surface 242. The anterior surface faces away from eye 210, while posterior surface 242 faces toward eye 210 when scleral lens 208 is positioned on eye 210. In some illustrative embodiments, the curvature of optical section 236 may be increased or decreased based on a desired optical power of scleral lens 208.

Lens manufacturing process 224 then identifies alteration 244 to wavefront 218 caused by wavefront 218 traveling into eye 210 through pupil 214. In this illustrative embodiment, lens manufacturing process 224 identifies alteration 244 by identifying difference 246 in optical paths 248 traveled by wavefront 218 as compared to other wavefronts in plurality of wavefronts 216 entering eye 210. Optical paths 248 are the direction and speed traveled by wavefront 218 as wavefront travels into eye 210 through pupil 214.

Difference 246 in optical paths 248 is caused by inconsistency 222 in pupil 214. For example, inconsistency 222 may cause wavefront 218 entering through a first area in plurality of areas 250 of pupil 214 to slow down more than a second wavefront entering through a second area in plurality of areas 250. In the illustrative embodiments, lens manufacturing process 224 identifies difference 246 using aberrometer 252.

Aberrometer 252 is a sensor that measures difference 246 in optical paths 248 traveled by plurality of wavefronts 216. In the illustrative embodiments, aberrometer 252 expresses difference 246 using Zernike polynomials 254. Zernike polynomials 254 is a set of polynomials that are orthogonal over the unit circle. Zernike polynomials 254 are defined with polar coordinates in this illustrative embodiment, for example, a radial coordinate and an azimuthal component. The radial coordinate is a polynomial, and the azimuthal coordinate is sinusoidal.

Each Zernike polynomial 254 expressed by aberrometer 252 represents a different aberration for pupil 214. For example, the Zernike polynomial representing the lower order aberration of Sphere is $2\rho^2-1$, where $\rho$ is the radial coordinate of the Zernike polynomial. Lens manufacturing process 224 receives coefficients 256 from aberrometer 252, where each coefficient represents the contribution of the particular Zernike polynomial to inconsistency 222.

Lens manufacturing process 224 then uses coefficients 256 to identify difference 246 in optical paths 248. Difference 246 is expressed by lens manufacturing process 224 in terms of differences from a reference plane for inconsistency 222, such as reference plane 232. In this illustrative embodiment, lens manufacturing process 224 generates a value for the optical path difference in air caused by the aberration at point $\rho$ at azimuth $\theta$, which is the product of a corresponding Zernike polynomial in Zernike polynomials 254 and a corresponding coefficient in coefficients 256. Lens manufacturing process 224 then sums the optical path differences for the point $\rho$ at azimuth $\theta$.

Lens manufacturing process 224 then generates modification 258 to be made to posterior surface 242 of optical section 236 that equalizes difference 246. In other words, lens manufacturing process 224 generates modification 258 that causes optical paths 248 traveled by plurality of wavefronts 216 to be substantially equal. In the illustrative embodiments, modification 258 is a change in thickness 260 to material 264 for area 262 on posterior surface 242 of optical section 236. For example, modification 258 may be a reduction in thickness 260 of material 264 in area 262 when wavefront 218 traveling through the corresponding location on pupil 214 travels at a slower speed than other locations on pupil 214. In another illustrative example, lens manufacturing process 224 generates the reduction in thickness 260 of material 264 in area 262 by reducing the sag value for the curve of material 264, according to number of dimensions 226, by the sum of the optical path differences for the point $\rho$ at azimuth $\theta$.

Lens manufacturing process 224 uses the index of refraction of material 264 and the index of refraction of the substance to be in space 240 to generate modification 258. In this illustrative embodiment, lens manufacturing process 224 calculates $(1-n_1)/(n_1-n_2)$, where 1 is the index of refraction of air, $n_1$ is the index of refraction for material 264, and $n_2$ is the index of refraction of the air, tear film, or other suitable substance located in space 240. Lens manufacturing process 224 then adds or subtracts the values for each point in number of dimensions 226, such as the distances for optical section 236 from reference plane 232.

In some illustrative embodiments, lens manufacturing process 224 also generates additional modifications to equalize difference 246 when pupil 214 changes size. For example, pupil 214 may increase in size as ambient light decreases in intensity. In such illustrative embodiments, lens manufacturing process 224 extrapolates modification 258 for a larger radius of pupil 214. For example, lens manufacturing process 224 may generate additional values using modification 258 and an n-th order polynomial, such as a third order polynomial. In one illustrative example, lens manufacturing process 224 uses a curve fitting algorithm, such as the Levenberg-Marquardt algorithm to generate additional values.

Once lens manufacturing process 224 generates modification 258, lens manufacturing process 224 generates plurality of computer numeric control codes 268, where plurality of computer numeric control codes 268 include codes that cause a manufacturing system to apply modification 258 to posterior surface 242 of optical section 236 of scleral lens 208. For example, plurality of computer numeric control codes 268 may include codes and/or instructions that cause lens manufacturing system 206 to apply modification 258.

In this illustrative embodiment, lens manufacturing process 224 then sends plurality of computer numeric control codes 268 to controller 270 of lens manufacturing system 206. Controller 270 may be computer system 272 in an illustrative embodiment. An example implementation of computer system 272 is data processing system 900 in FIG. 9. Controller 270 receives plurality of computer numeric control codes 268 and causes tool 274 to operate as designated by plurality of computer numeric control codes 268. In this illustrative embodiment, tool 274 is lathe 276. Lathe 276 is an apparatus that rotates scleral lens 208 while posterior surface 242 contacts lathe 276. Controller 270 may change the speed of rotation and move lathe 276 toward or away from scleral lens 208 in this illustrative example. Of course, in other illustrative embodiments, other tools may be used.

Once scleral lens 208 is manufactured, scleral lens 208 may be positioned on eye 210. Light 278 then enters pupil 214 through optical section 236 of scleral lens 208 and inconsistency 222. In this illustrative embodiment, difference 246 caused by inconsistency 222 is reduced or equalized. In other words, the optical paths traveled by wavefront 280 and wavefront 282 of light 278 have substantially no difference in optical paths.

The illustration of computer system 202 in lens manufacturing environment 200 is not meant to imply physical or architectural limitations to the manner in which different features may be implemented. Other components in addition to and/or in place of the ones illustrated may be used. Some components may be unnecessary in some illustrative embodiments. Also, the blocks are presented to illustrate some functional components. One or more of these blocks may be combined and/or divided into different blocks when implemented in different illustrative embodiments.

For example, lens manufacturing system 206 may include computer system 202. More specifically, computer system 202 may also be controller 270 in some illustrative embodiments. In these illustrative embodiments, computer system 202 communicates with optical coherence tomography scanner 235 and aberrometer 252 using a network, such as a transmission control protocol/Internet protocol (TCP/IP) network.

Figure 3:
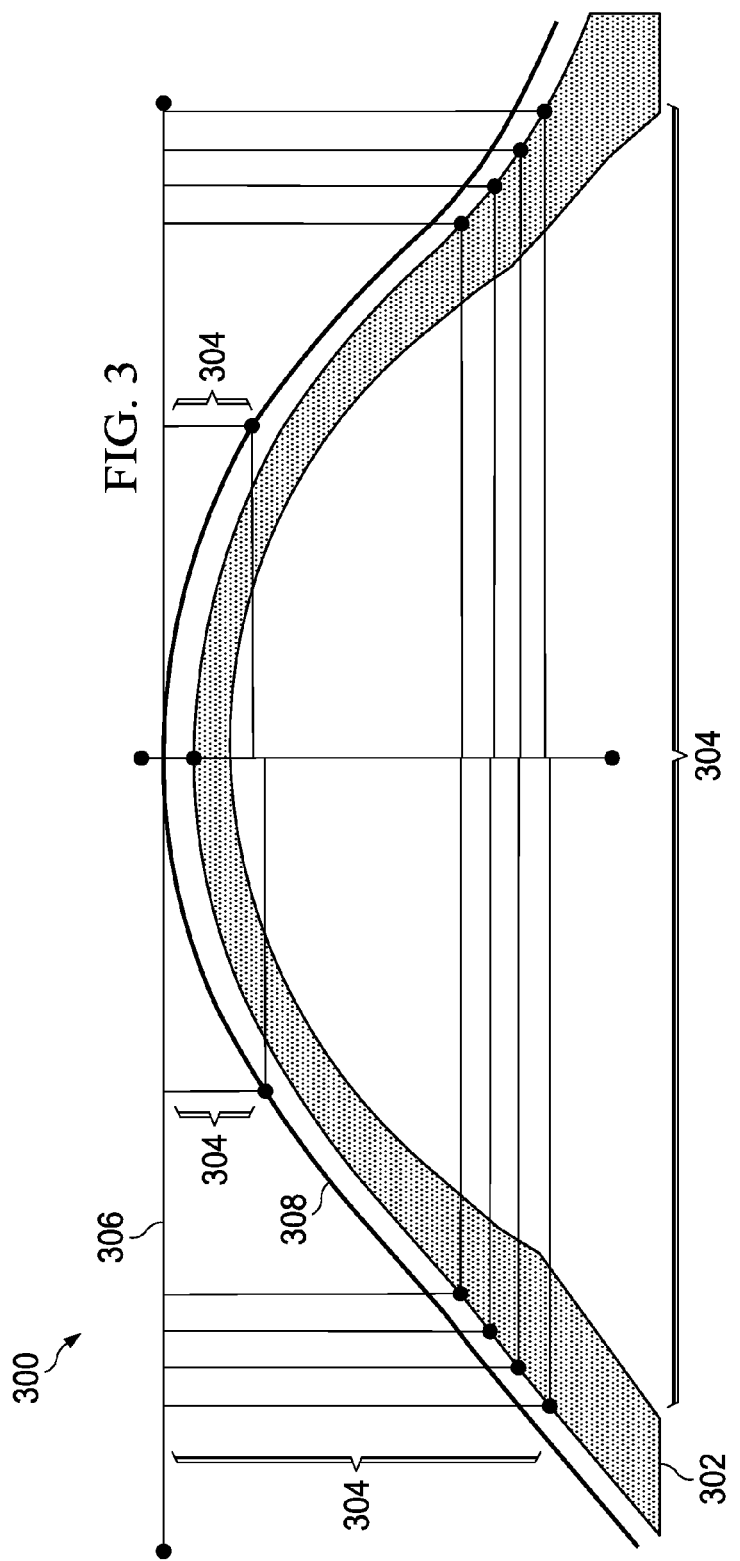
FIG. 3 depicts an illustration of an optical coherence tomography scan in accordance with an illustrative embodiment.

With reference now to FIG. 3, an illustration of an optical coherence tomography scan is depicted in accordance with an illustrative embodiment. Optical coherence tomography scan 300 is an example implementation of an optical coherence tomography scan in number of optical coherence tomography scans 230 in FIG. 2.

Optical coherence tomography scan 300 is generated by an optical coherence tomography scanner, such as optical coherence tomography scanner 235 in FIG. 2. Optical coherence tomography scan 300 includes eye 302. Optical coherence tomography scan 300 also includes measurements 304. Measurements 304 are generated by identifying light that is backscattered from eye 302. More specifically, measurements 304 are the distances from reference plane 306 to eye 302 at each location on eye 302. Reference plane 306 is an example of reference plane 232 in FIG. 2.

A lens manufacturing process, such as lens manufacturing process 224 in FIG. 2, uses measurements 304 of the distances from reference plane 306 to eye 302 to generate a number of dimensions for a scleral lens to be manufactured and positioned on eye 302. In this illustrative embodiment, the process generates number of dimensions 308 as the dimensions of a scleral lens for eye 302. Number of dimensions 308 is an example of number of dimensions 226 in FIG. 2.

Turning now to FIG. 4, an illustration of coefficients for Zernike polynomials is depicted in accordance with an illustrative embodiment. Coefficients 404 in table 400 are examples of coefficients 256 in FIG. 2. While table 400 is presented as a table in this illustration, coefficients 404 may be stored and/or presented in another form, such as a linked list, database, or another suitable data structure.

In this illustrative example, coefficients 404 in table 400 are received by a lens manufacturing process from an aberrometer, such as aberrometer 252 in FIG. 2. Coefficients 404 represent the contribution of each Zernike polynomial to the representation of the inconsistencies in the eye. For example, entry 402 is an example of a coefficient for the first Zernike polynomial.

In other words, each Zernike polynomial is a mathematical description of a different type of aberration that occurs at different locations in the eye. Coefficients 404 are numbers that indicate the relative contribution of the aberration described by the corresponding Zernike polynomial to the inconsistencies of the eye. For example, entry 402 indicates that the first Zernike polynomial has a coefficient of −0.6675799289. Entry 402 indicates that the deviation of a wavefront from the reference wave for the first mode of the Zernike polynomial is −0.6675799289 taken times the polynomial equation for the aberration of index number 1 or y-tilt.

With reference now to FIG. 5, an illustration of a modification represented in table form is depicted in accordance with an illustrative embodiment. Modification table 500 is an example of a table representation of modification 258 in FIG. 2.

In this illustrative embodiment, column 502 represents a particular pupil radius. Column 504 indicates the radial coordinate of the pupil, represented as $\rho$. The radial coordinate of the pupil is the distance from a reference point or the center of the pupil for which the values in the particular row are generated. Column 506 indicates the azimuthal angle from a reference point for which the values in the particular row are generated. Columns 508 represent the differences in optical paths, such as difference 246 in FIG. 2 traveled by wavefronts at the corresponding pupil radius in column 502, radial coordinate in column 504, and azimuthal angle in column 506. Columns 508 are generated by multiplying the respective Zernike coefficient by the polynomial for the indexed aberration for each value of $\rho,\theta$. For example, the cell F5 in modification table 500 is generated using the second Zernike polynomial. More specifically, the value in F5 is generated by calculating: F2*2*B5*cos(C2) to generate the value of 0.0054977.

Once columns 508 are generated, a lens manufacturing process generates column 510, which indicates a sum of the differences in optical path for each pupil radius and radial coordinate from columns 502 and 504, respectively. Column 510 represents the sums in microns, while column 512 represents the sums in millimeters.

Figure 6:
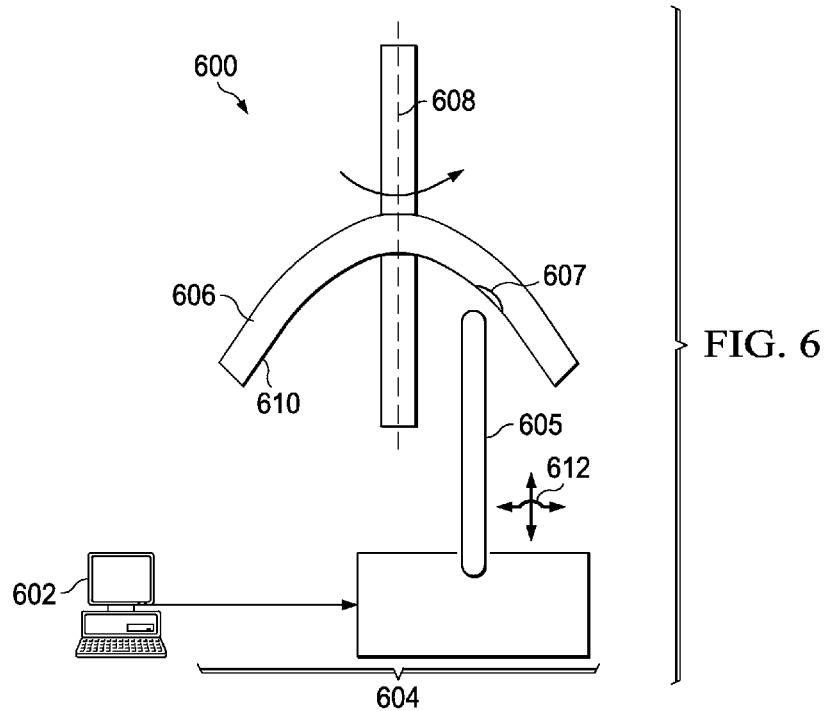
FIG. 6 depicts an illustration of a lens manufacturing system in accordance with an illustrative embodiment.

Looking now to FIG. 6, an illustration of a lens manufacturing system is depicted in accordance with an illustrative embodiment. Lens manufacturing system 600 is an example implementation of lens manufacturing system 206 in FIG. 2.

Lens manufacturing system 600 includes controller 602, lathe 604, and scleral lens 606. Controller 602 is an example of controller 270 in FIG. 2. In this illustrative embodiment, controller 602 is a computer system, such as data processing system 900 in FIG. 9.

Controller 602 causes lathe 604 to apply modification 607 to scleral lens 606. Modification 607 is an example of modification 258 in FIG. 2. Lathe 604 is an example of lathe 276 in FIG. 2. Controller 602 causes lathe 604 to engage and disengage. Lathe 604 contacts scleral lens 606 such that when lathe 604 is engaged, lathe 604 rotates scleral lens 606 along longitudinal axis 608.

Tool 605 is an object that removes material from scleral lens 606 when lathe 604 is rotating scleral lens 606 and tool 605 is in contact with posterior surface 610 of scleral lens 606. Controller 602 also causes tool 605 to move in directions 612 according to instructions received by controller. For example, controller 602 may receive a plurality of computer numeric control codes, such as plurality of computer numeric control codes 268 in FIG. 2.

By moving tool 605 in directions 612, controller 602 may cause tool 605 to contact or not contact posterior surface 610. Controller 602 may also move tool 605 in directions to apply a modification to different portions of posterior surface 610.

Figure 7:
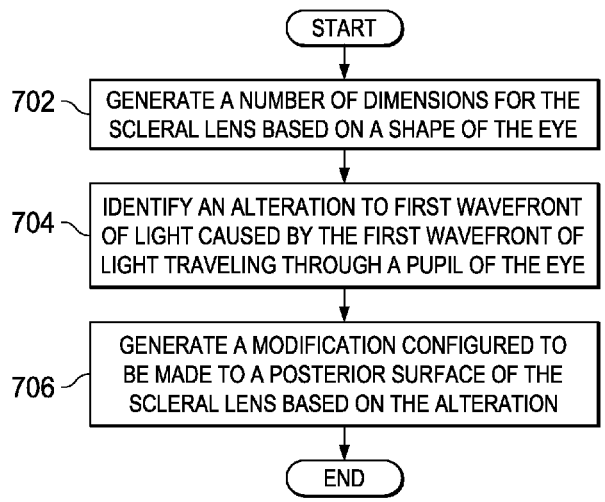
FIG. 7 depicts an illustration of a flowchart of a process for manufacturing a scleral lens in accordance with an illustrative embodiment.

With reference now to FIG. 7, an illustration of a flowchart of a process for manufacturing a scleral lens is depicted in accordance with an illustrative embodiment. The process may be performed by lens manufacturing process 224 and/or lens manufacturing system 206 in FIG. 2.

The process begins by generating a number of dimensions for the scleral lens based on a shape of an eye (step 702). The number of dimensions may be number of dimensions 226 in FIG. 2. The process may generate the number of dimensions using a number of optical coherence tomography (OCT) scans, such as number of optical coherence tomography scans 230 in FIG. 2. The number of optical coherence tomography scans may be performed to determine the distance to the eye from points on a reference plane, such as reference plane 232 in FIG. 2.

The process then identifies an alteration to a first wavefront of light caused by the first wavefront of light traveling through a pupil of the eye (step 704). The process may identify the alteration using Zernike polynomials and/or coefficients for the Zernike polynomials from an aberrometer. For example, the process may receive coefficients 256 from aberrometer 252 in FIG. 2. The process may then use the coefficients to identify a difference in optical paths traveled by wavefronts of light traveling into the pupil. The difference in optical paths is caused by an inconsistency in the pupil in this illustrative embodiment.

The process then generates a modification configured to be made to a posterior surface of the scleral lens based on the alteration (step 706). The process generates the modification by generating a change in the thickness of an optical section of a scleral lens to be manufactured and positioned on the eye. For example, the process may generate modification 258 for thickness 260 of posterior surface 242 of optical section 236 in FIG. 2. In the illustrative embodiments, the modification removes the alteration for a second wavefront of light traveling through the scleral lens and the pupil of the eye. For example, the modification to the thickness of the optical section of the scleral lens may increase or reduce the rate at which wavefront travels through the pupil. The process terminates thereafter.

Figure 8:
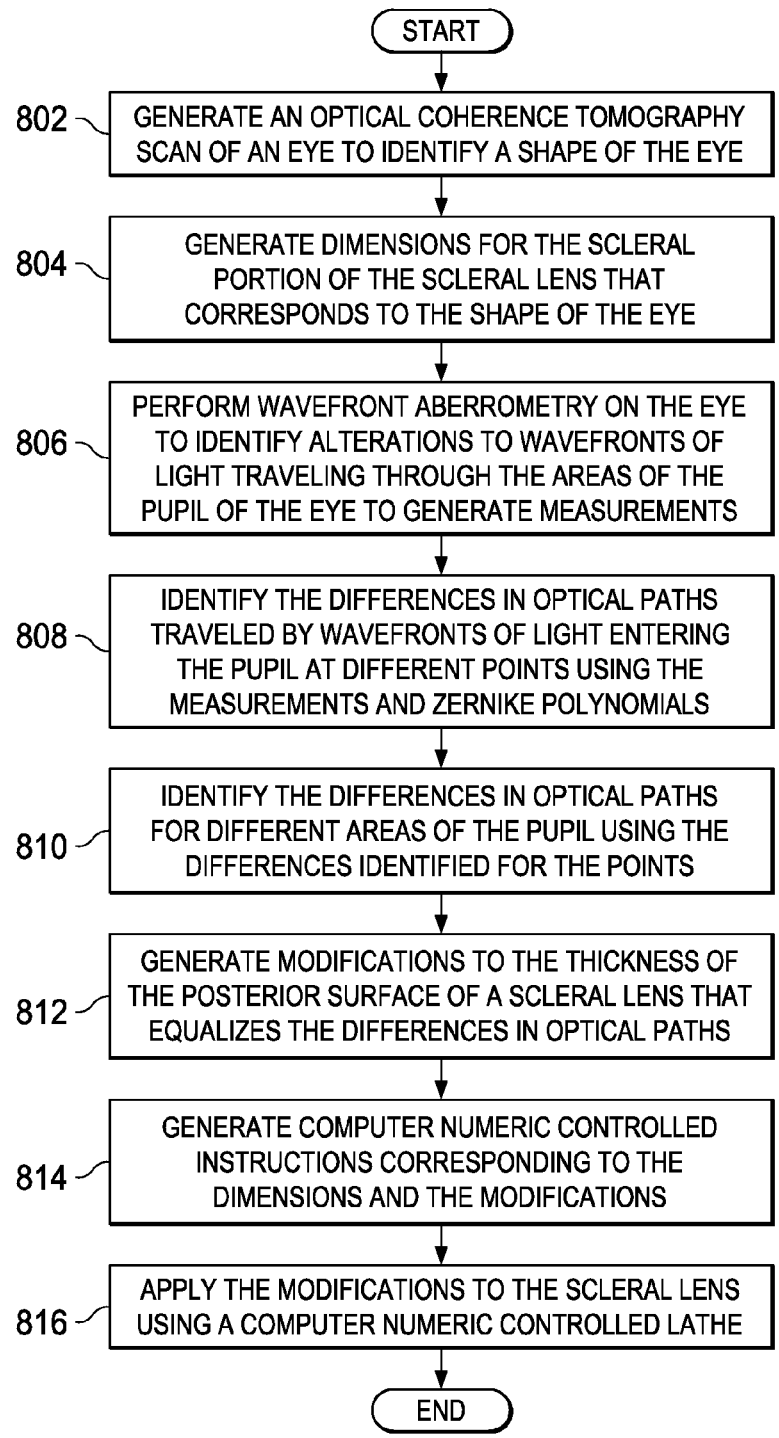
FIG. 8 depicts an illustration of a flowchart of a process for reducing higher order aberrations in an eye in accordance with an illustrative embodiment.

Looking now to FIG. 8, an illustration of a flowchart of a process for reducing higher order aberrations in an eye is depicted in accordance with an illustrative embodiment. The process may be performed by lens manufacturing process 224 and/or lens manufacturing system 206 in FIG. 2.

The process begins by generating an optical coherence tomography (OCT) scan of an eye to identify a shape of the eye (step 802). The process then generates dimensions for the scleral portion of the scleral lens that correspond to the shape of the eye (step 804). The process then performs wavefront aberrometry on the eye to identify alterations to wavefronts of light traveling through the areas of the pupil of the eye to generate measurements (step 806).

The process then identifies the differences in optical paths traveled by wavefronts of light entering the pupil at different points using the measurements and Zernike polynomials (step 808). The differences in optical paths are differences in optical path lengths in the illustrative embodiments. The process then identifies the differences in optical paths for additional areas of the pupil using the differences identified for the points in step 808 (step 810). The process then generates modifications to the thickness of the posterior surface of a scleral lens that equalize the differences in optical paths (step 812). Next, the process generates computer numeric controlled (CNC) instructions corresponding to the dimensions and the modifications (step 814). The process then applies the modifications to the scleral lens using a computer numeric controlled lathe (step 816). The process terminates thereafter.

In some illustrative embodiments, however, the process is repeated, at least in part, for additional Zernike polynomials. For example, the process identifies the differences in optical paths traveled by a portion of the wavefronts of light entering the pupil using Zernike polynomials. After performing step 816, the process may return to step 808 and identify the differences in optical paths for additional wavefronts using additional Zernike polynomials. The process may be repeated until a desired amount of reduction in aberrations is reached.

Turning now to FIG. 9, a diagram of a data processing system is depicted in accordance with an illustrative embodiment. In this illustrative example, data processing system 900 includes communications fabric 902, which provides communications between processor unit 904, memory 906, persistent storage 908, communications unit 910, input/output (I/O) unit 912, and display 914. Data processing system 900 is an example of a data processing system that runs a lens manufacturing process, such as lens manufacturing process 224 in FIG. 2.

Processor unit 904 serves to process instructions for software that may be loaded into memory 906. Processor unit 904 may be a number of processors, a multi-processor core, or some other type of processor, depending on the particular implementation. A "number", as used herein, with reference to an item, means "one or more items". Further, processor unit 904 may be implemented using a number of heterogeneous processor systems in which a main processor is present with secondary processors on a single chip. As another illustrative example, processor unit 904 may be a symmetric multi-processor system containing multiple processors of the same type.

Memory 906 and persistent storage 908 are examples of storage devices 916. A storage device is any piece of hardware that is capable of storing information, such as, for example without limitation, data, program code in functional form, and/or other suitable information either on a temporary basis and/or a permanent basis. Memory 906, in these examples, may be, for example, a random access memory or any other suitable volatile or non-volatile storage device. Persistent storage 908 may take various forms depending on the particular implementation. For example, persistent storage 908 may contain one or more components or devices. For example, persistent storage 908 may be a hard drive, a flash memory, a rewritable optical disk, a rewritable magnetic tape, or some combination of the above. The media used by persistent storage 908 also may be removable. For example, a removable hard drive may be used for persistent storage 908.

Communications unit 910, in these examples, provides for communications with other data processing systems or devices. In these examples, communications unit 910 is a network interface card. Communications unit 910 may provide communications through the use of either or both physical and wireless communications links.

Input/output unit 912 allows for input and output of data with other devices that may be connected to data processing system 900. For example, input/output unit 912 may provide a connection for user input through a keyboard, a mouse, and/or some other suitable input device. Further, input/output unit 912 may send output to a printer. Display 914 provides a mechanism to display information to a user.

Instructions for the operating system, applications and/or programs may be located in storage devices 916, which are in communication with processor unit 904 through communications fabric 902. In these illustrative examples, the instructions are in a functional form on persistent storage 908. These instructions may be loaded into memory 906 for execution by processor unit 904. The processes of the different embodiments may be performed by processor unit 904 using computer implemented instructions, which may be located in a memory, such as memory 906.

These instructions are referred to as program code, computer usable program code, or computer readable program code that may be read and processed by a processor in processor unit 904. The program code in the different embodiments may be embodied on different physical or computer readable storage media, such as memory 906 or persistent storage 908.

Program code 918 is located in a functional form on computer readable media 920 that is selectively removable and may be loaded onto or transferred to data processing system 900 for execution by processor unit 904. Program code 918 and computer readable media 920 form computer program product 922 in these examples. In one example, computer readable media 920 may be computer readable storage media 924 or computer readable signal media 926. Computer readable storage media 924 may include, for example, an optical or magnetic disc that is inserted or placed into a drive or other device that is part of persistent storage 908 for transfer onto a storage device, such as a hard drive that is part of persistent storage 908. Computer readable storage media 924 also may take the form of a persistent storage, such as a hard drive, a thumb drive, or a flash memory that is connected to data processing system 900. In some instances, computer readable storage media 924 may not be removable from data processing system 900. In these illustrative examples, computer readable storage media 924 is a non-transitory computer readable storage media.

Alternatively, program code 918 may be transferred to data processing system 900 using computer readable signal media 926. Computer readable signal media 926 may be, for example, a propagated data signal containing program code 918. For example, computer readable signal media 926 may be an electro-magnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some illustrative embodiments, program code 918 may be downloaded over a network to persistent storage 908 from another device or data processing system through computer readable signal media 926 for use within data processing system 900. For instance, program code stored in a computer readable storage medium in a server data processing system may be downloaded over a network from the server to data processing system 900. The data processing system providing program code 918 may be a server computer, a client computer, or some other device capable of storing and transmitting program code 918.

The different components illustrated for data processing system 900 are not meant to provide architectural limitations to the manner in which different embodiments may be implemented. The different illustrative embodiments may be implemented in a data processing system including components in addition to or in place of those illustrated for data processing system 900. Other components shown in FIG. 9 can be varied from the illustrative examples shown. The different embodiments may be implemented using any hardware device or system capable of executing program code. As one example, the data processing system may include organic components integrated with inorganic components, and/or may be comprised entirely of organic components, excluding a human being. For example, a storage device may be comprised of an organic semiconductor.

As another example, a storage device in data processing system 900 is any hardware apparatus that may store data. Memory 906, persistent storage 908 and computer readable media 920 are examples of storage devices in a tangible form.

In another example, a bus system may be used to implement communications fabric 902 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 906 or a cache, such as found in an interface and memory controller hub that may be present in communications fabric 902.

The different illustrative embodiments allow a scleral lens to be manufactured to reduce or eliminate higher order aberrations in an eye. The scleral lens may be manufactured with greater differences in thickness between modifications. Such differences allow the lenses to be manufactured with higher tolerances than modifications with lesser differences, which reduce the cost of manufacture. Further, the modifications applied to the posterior surface of the scleral lens are less variable in effectiveness as compared to modifications applied to the anterior surface of a lens because conditions of the eye, such as tear film thickness and eye dryness do not change the effects of the posterior surface modifications on the wavefronts of light traveling through the lens and the pupil of the eye.

Case Study #1

A young adult female underwent bilateral LASIK surgery one year prior. She subsequently suffered an acute inflammation in one eye that caused an irregular astigmatism. The irregular astigmatism could not be fully with conventional eyeglasses, and her best corrected vision in that eye was 20/30 with a rigid contact lens. This condition made it difficult for her to function.

A scleral lens with conventional sphero-cylindrical optics was designed. Without the lens, the total higher order aberration RMS was 4.040, coma was 2.035, spherical aberrations was 3.116 microns, and trefoil was 1.051 microns. With a conventional scleral lens with classical sphero-cylindrical optics, the aberrations measured 1.160 microns total (71% reduction), 0.750 microns of coma (63% reduction), 0.837 microns of spherical aberration (73% reduction), and 0.200 microns of trefoil (81% reduction). Another scleral lens was made according to the illustrative embodiments resulting in further reductions in aberrations compared to the conventional scleral lens: 34% reduction in total aberrations, 63% reduction in coma, and 12% reduction in spherical aberration. The resulting Snellen visual acuity with the enhanced scleral lens was 20/10+.

Case Study #2

A young adult female who had bilateral LASIK 6 years prior, had been fitted with rigid scleral lenses but was only able to achieve 20/30 best corrected vision in her left eye. Without a lens in her left eye, aberrations were: 1.227 microns total RMS, 0.441 microns of coma, and 1.112 microns of spherical aberration. Aberrations were significantly reduced with a scleral lens having conventional optics: 56% reduction in total RMS, 17% reduction in coma, and a 75% reduction in spherical aberration. An enhanced scleral lens with the current embodiments resulted in the following improvements compared to the conventional scleral lens: 54% reduction in total RMS, 50% reduction in coma, and a 66% reduction in spherical aberration. Corrected visual acuity improved from 20/30 to 20/15+.

Case Study #3

An adult male had bilateral LASIK approximately 10 years ago and developed keratectasia, a condition similar to keratoconus in that the cornea progressively steepens. The patient had been fitted with rigid scleral lenses, with best-corrected visual acuity of 20/25 in the left eye. Without lens, his higher order aberrations in the left eye measured: 2.766 microns total RMS, 2.474 microns of coma, and 0.237 microns of spherical aberration. With his conventional scleral lenses, aberrations were reduced by: 39% for total RMS and 69% for coma. There was a paradoxical increase in spherical aberration with his lens of 84%. An enhanced scleral lens with current embodiments reduced the aberrations compared to the conventional lens as follows: 24% reduction in total RMS, 63% reduction in coma, and 19% reduction in spherical aberration. Corrected visual acuity improved to 20/20.

Thus, the different illustrative embodiments provide a method, computer program product, and apparatus for manufacturing a scleral contact lens. A number of dimensions for the scleral lens is generated based on a shape of an eye. An alteration to a first wavefront of light caused by the first wavefront of light traveling through a pupil of the eye is identified. A modification configured to be made to a posterior surface of the scleral lens is generated based on the alteration. The modification removes the alteration for a second wavefront of light traveling through the scleral lens and the pupil of the eye.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiment. The terminology used herein was chosen to best explain the principles of the embodiment, the practical application or technical improvement over technologies found in the marketplace, or to enable others of ordinary skill in the art to understand the embodiments disclosed here.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A method for manufacturing a scleral lens, the method comprising:
generating a number of dimensions for the scleral lens based on a shape of an eye;
identifying an alteration to a first wavefront of light caused by the first wavefront of light traveling through a pupil of the eye and the scleral lens; and
generating a modification configured to be made to a surface of the scleral lens based on the alteration, wherein the modification removes the alteration for the first wavefront of light traveling through the scleral lens and the pupil of the eye.

2. The method of claim 1, further comprising:
applying the modification to a posterior surface of the scleral lens; and
wherein the modification removes the alteration for a second wavefront of light traveling through the scleral lens and the pupil of the eye.

3. The method of claim 2, wherein generating the modification configured to be made to the posterior surface of the second portion of the scleral lens based on the alteration comprises:
identifying a thickness of a portion of the scleral lens for each of the plurality of areas that equalizes the difference in the number of optical paths.

4. The method of claim 2, wherein applying the modification to the posterior surface of the scleral lens comprises:
removing material from the posterior surface of the scleral lens according to the modification.

5. The method of claim 1, wherein identifying the alteration to the first wavefront of light caused by the first wavefront of light traveling through the pupil of the eye comprises:
identifying a difference in a plurality of optical paths traveled by the light as the light travels through a plurality of areas of the pupil of the eye to form the alteration to the first wavefront of light.

6. The method of claim 1, wherein the scleral lens comprises an optical section and a scleral section.

7. The method of claim 6, wherein the modification is configured to be made to a posterior surface of the optical section of the scleral lens, and further comprising:
positioning the scleral section of the scleral lens in contact with a sclera of the eye, wherein a space is present between the optical section of the scleral lens and the eye.

8. The method of claim 1, wherein the alteration is generated by the wavefront of light traveling through an inconsistency in the pupil of the eye.

9. An apparatus comprising:
a tool configured to remove material from a posterior surface of a scleral lens; and
a controller configured to receive a modification to be made to a surface of the scleral lens and operate the tool to apply the modification to the surface of the scleral lens, wherein the modification removes an alteration to a wavefront of light caused by the wavefront of light traveling through a pupil of an eye.

10. The apparatus of claim 9, wherein the tool is configured to remove the material from a posterior surface of the scleral lens and further comprises the tool being configured to reduce a thickness of the scleral lens.

11. The apparatus of claim 10, wherein the controller being configured to operate the tool to apply the modification to the posterior surface of the lens comprises the controller being configured to operate the tool to reduce a thickness of the scleral lens.

12. The apparatus of claim 11, wherein the controller comprises a computer system.

13. The apparatus of claim 10, wherein the modification is applied to the posterior surface of an optical section of the scleral lens.

14. The apparatus of claim 10, wherein the controller being configured to operate the tool to apply the modification to the posterior surface of the scleral lens comprises the controller being configured to cause the lathe to move to a position, engage the lathe, and disengage the lathe.

15. The apparatus of claim 9, wherein the tool is a lathe.

16. The apparatus of claim 9, wherein the modification comprises a plurality of computer numerical control codes.

17. A computer program product comprising:
a computer readable storage medium;
program instructions, stored on the computer readable storage medium, for generating a number of dimensions for a scleral lens based on a shape of an eye;
program instructions, stored on the computer readable storage medium, for identifying an alteration to a first wavefront of light caused by the first wavefront of light traveling through a pupil of the eye and the scleral lens; and
program instructions, stored on the computer readable storage medium, for generating a modification configured to be made to a surface of the scleral lens based on the alteration, wherein the modification removes the alteration for a second wavefront of light traveling through the scleral lens and the pupil of the eye.

18. The computer program product of claim 17, wherein the program instructions, stored on the computer readable storage medium, for identifying the alteration to the first wavefront of light caused by the first wavefront of light traveling through the pupil of the eye and the scleral lens comprise:
program instructions, stored on the computer readable storage medium, for identifying a difference in a plurality of optical paths traveled by the light as the light travels through a plurality of areas of the pupil of the eye to form the alteration to the first wavefront of light.

19. The computer program product of claim 18, wherein the program instructions, stored on the computer readable storage medium, for generating the modification configured to be made to the posterior surface of the second portion of the scleral lens based on the alteration comprise:
program instructions, stored on the computer readable storage medium, for identifying a thickness of a portion of the scleral lens for each of the plurality of areas that equalizes the difference in the number of optical paths.

20. The computer program product of claim 17, wherein the scleral lens comprises an optical section and a scleral section.

* * * * *